(12) United States Patent
Pollack

(10) Patent No.: US 9,251,393 B2
(45) Date of Patent: Feb. 2, 2016

(54) BARCODE READING TEST TUBE HOLDER

(71) Applicant: Benjamin Samuel Pollack, Budd Lake, NJ (US)

(72) Inventor: Benjamin Samuel Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/376,117

(22) PCT Filed: Feb. 1, 2013

(86) PCT No.: PCT/US2013/024362
§ 371 (c)(1),
(2) Date: Jul. 31, 2014

(87) PCT Pub. No.: WO2013/116661
PCT Pub. Date: Aug. 8, 2013

(65) Prior Publication Data
US 2014/0374480 A1    Dec. 25, 2014

Related U.S. Application Data

(60) Provisional application No. 61/594,491, filed on Feb. 3, 2012.

(51) Int. Cl.
| | |
|---|---|
| *G06K 7/10* | (2006.01) |
| *B01L 9/06* | (2006.01) |
| *B01L 3/00* | (2006.01) |
| *G06K 7/015* | (2006.01) |
| *G01N 35/00* | (2006.01) |
| *G01N 35/04* | (2006.01) |

(52) U.S. Cl.
CPC ........... *G06K 7/10871* (2013.01); *B01L 3/5453* (2013.01); *B01L 9/06* (2013.01); *G01N 35/04* (2013.01); *G06K 7/015* (2013.01); *G06K 7/10831* (2013.01); *B01L 2300/021* (2013.01); *B01L 2300/168* (2013.01); *G01N 2035/00752* (2013.01); *G01N 2035/0406* (2013.01)

(58) Field of Classification Search
USPC ................... 235/440, 462.36, 375; 340/568.1
See application file for complete search history.

(56) References Cited

U.S. PATENT DOCUMENTS

| | | | | |
|---|---|---|---|---|
| 5,210,398 | A | * | 5/1993 | Metlitsky ................. 235/462.24 |
| 5,726,433 | A | * | 3/1998 | Peng ........................ 235/462.36 |

(Continued)

FOREIGN PATENT DOCUMENTS

| | | |
|---|---|---|
| EP | 2316570 A2 | 5/2011 |
| JP | 2011242167 A | 12/2011 |

OTHER PUBLICATIONS

PCT International Search Report and Written Opinion dated Apr. 12, 2013 (8 Pages).

(Continued)

*Primary Examiner* — Allyson Trail
(74) *Attorney, Agent, or Firm* — Pepper Hamilton LLP

(57) ABSTRACT

Tube holders for use in a lab environment include an optical device to allow the observation of barcode information on a sample tube. The optical device can include a lens or camera. Tube holders can also include reflective surfaces or mechanical mechanisms to allow the tube to be rotated such that reading a barcode does not require a strict initial orientation of the tube when placed in the tube holder. Arrays of tubes can include optical guides to allow barcodes to be read by an external imaging device.

26 Claims, 17 Drawing Sheets

(56) References Cited

U.S. PATENT DOCUMENTS

| | | | |
|---|---|---|---|
| 5,941,366 A * | 8/1999 | Quinlan et al. | 198/465.1 |
| 6,202,829 B1 | 3/2001 | Van Dyke, Jr. et al. | |
| 7,604,987 B2 * | 10/2009 | Hutmacher et al. | 435/298.1 |
| 8,741,655 B2 * | 6/2014 | Justin et al. | 436/47 |
| 2002/0038820 A1 | 4/2002 | Check et al. | |
| 2003/0179364 A1 | 9/2003 | Steenblik et al. | |
| 2007/0046464 A1 | 3/2007 | Onderko et al. | |
| 2007/0058156 A1 * | 3/2007 | Ando et al. | 356/28 |
| 2008/0121687 A1 * | 5/2008 | Buhot | 235/375 |
| 2008/0240991 A1 | 10/2008 | Wakamiya et al. | |
| 2009/0028754 A1 * | 1/2009 | Robb | 422/65 |
| 2011/0106312 A1 * | 5/2011 | Chen et al. | 700/259 |
| 2011/0316713 A1 * | 12/2011 | Okubo | 340/673 |
| 2013/0033381 A1 * | 2/2013 | Breed | 340/568.1 |
| 2014/0171829 A1 * | 6/2014 | Holmes et al. | 600/575 |

OTHER PUBLICATIONS

Extended EP Search Report dated Nov. 17, 2015 of corresponding European Patent Application No. 13744231.5, 5 Pages.

* cited by examiner

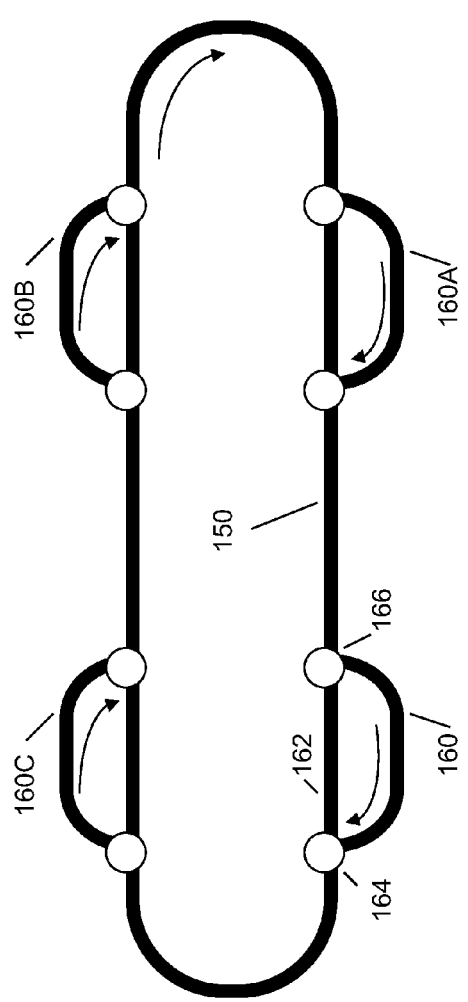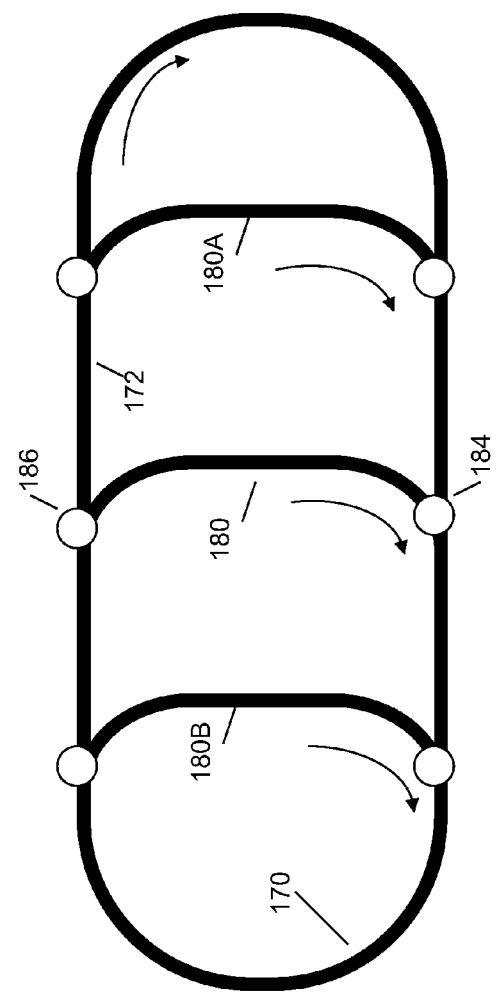

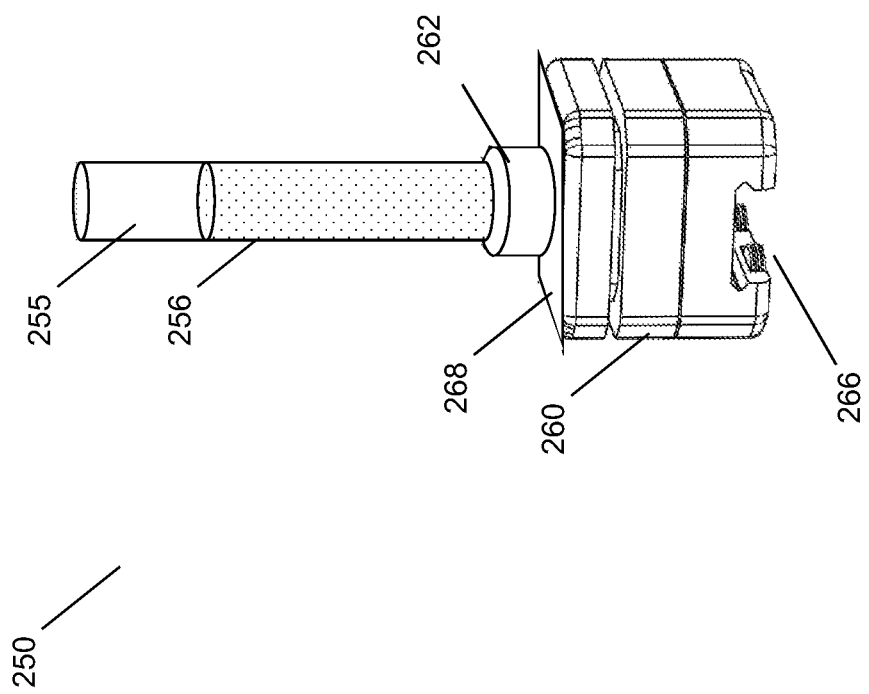

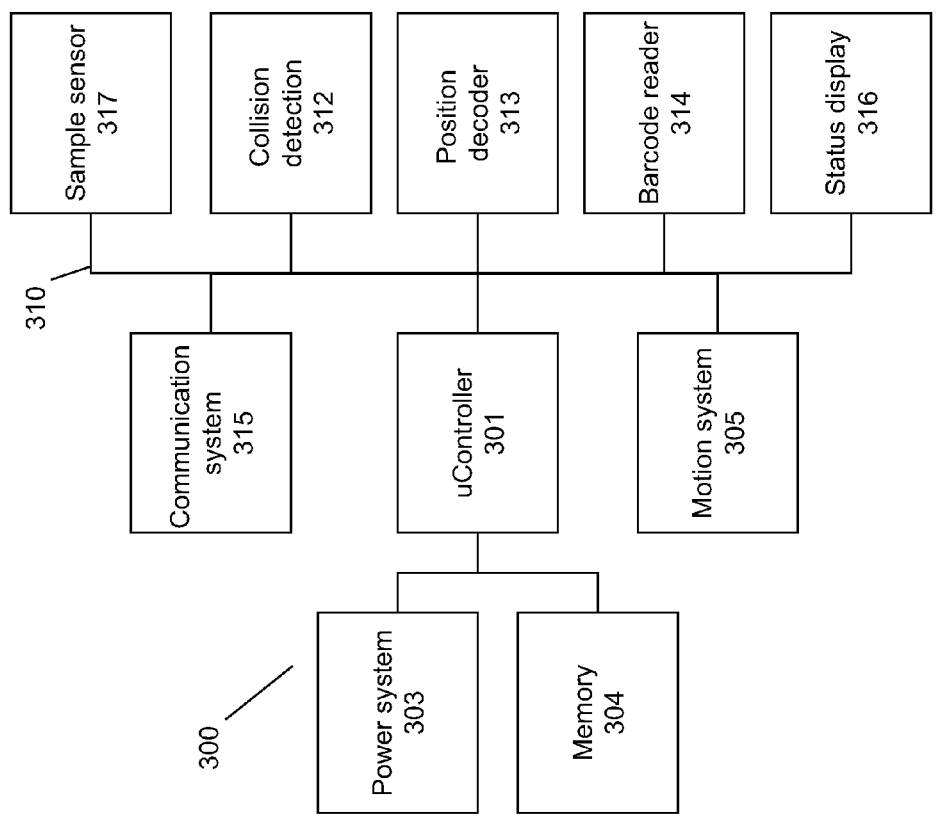

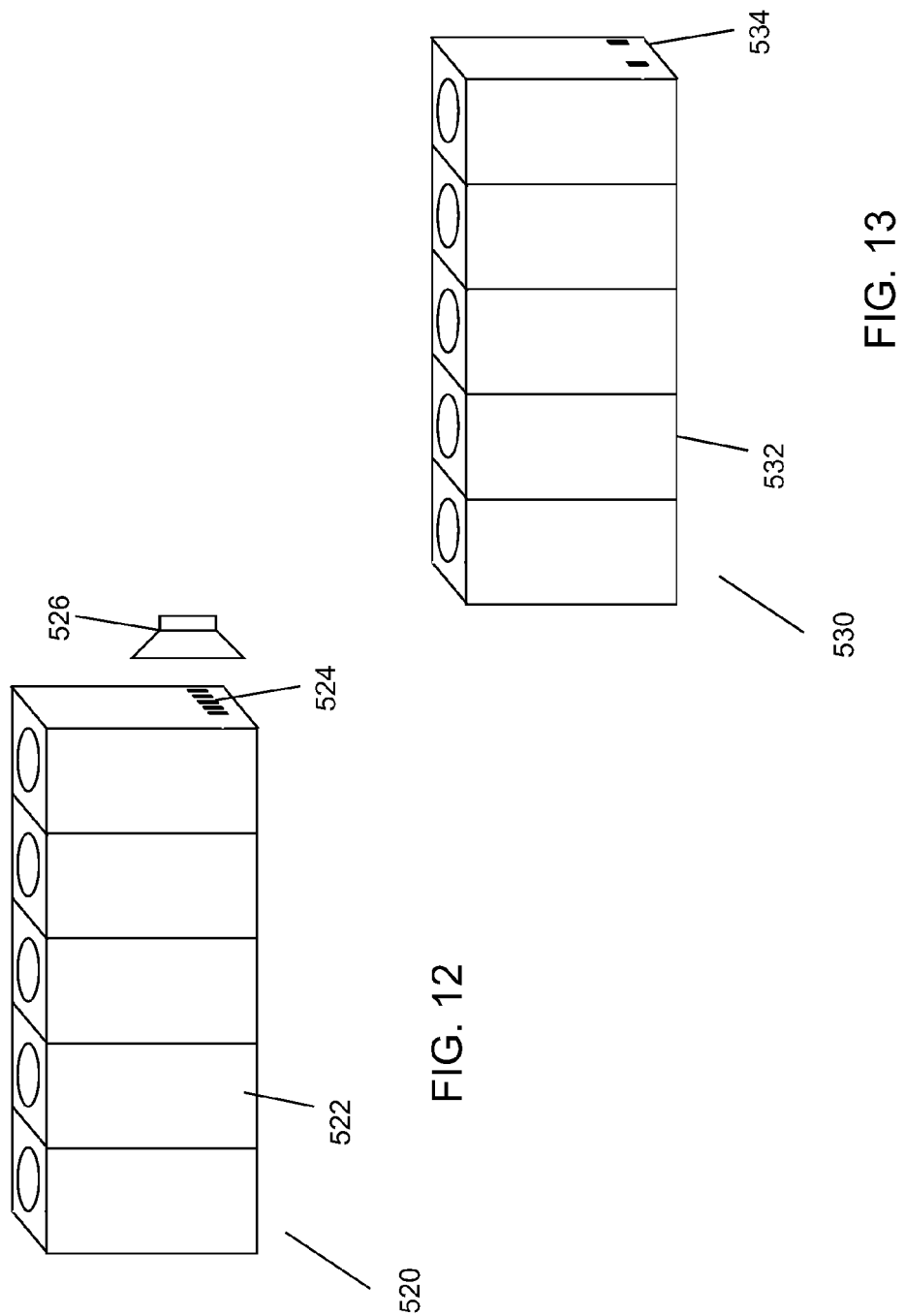

BARCODE READING TEST TUBE HOLDER

CROSS-REFERENCE TO RELATED APPLICATIONS

This application claims priority to U.S. provisional application Ser. No. 61/594,491 filed Feb. 3, 2012, which is incorporated herein by reference in its entirety.

TECHNOLOGY FIELD

The present invention relates in general to an automation system for use in a laboratory environment and, more particularly to systems and methods for transporting patient samples for in vitro diagnostics in a clinical analyzer via active transport devices. Embodiments of the present invention are particularly well suited, but in no way limited, to carriers and racks for transporting fluid samples in an in vitro diagnostics environment, having optical means for reading barcodes on fluid sample tubes.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. Samples can be identified by the analyzer, automation system, and operators using barcodes placed on each test tube carrying a sample. Barcodes can be placed using stickers when a fluid sample is obtained, such as in a hospital environment. An operator can take a sample tube and scan the barcode to pull up the identity of the sample on a terminal. When the sample is placed in a puck in the automation system, the puck can be rotated at points in the system to read the barcode. However, this requires round pucks as the entire puck is rotated. Similarly, when samples are placed into racks for transporting between machines or transporting within a machine, most racks have no ability to display barcodes for reading. Typically, samples must be removed from conventional racks before reading a barcode by hand. Some prior art racks include a window and a one-dimensional rack that allows a row of barcodes to be read, so long as each tube in the rack is oriented with the barcode in the window.

Currently, it is difficult to design an automation system without round pucks because of the need to obtain barcode information. Similarly, it would be desirable to allow tubes to be placed in racks without relying on the operator to orient each tube correctly in a desired direction, or in racks containing arrays of tubes. It is desirable to limit reliance on operators so that human error can be reduced.

SUMMARY

Embodiments of the present invention address and overcome one or more of the above shortcomings and drawbacks, by providing apparatus and systems for reading barcodes. These embodiments are particularly suitable for, but are not limited to, reading information of samples being moved in an in vitro diagnostics IVD environment.

Embodiments of the present invention may be directed to apparatus to make a barcode visible to view via optical means. The apparatus can include mechanical apparatus to rotate a sample tube, optical means to redirect the image of a barcode to one or more optical devices, and an arrangement of a plurality of optical devices to allow viewing of a barcode regardless of orientation. These apparatus can be included as part of a carrier or rack for handling sample tubes, expediting the barcode reading process.

According to one embodiment of the invention, a carrier for use in an in vitro diagnostics environment includes a tube holder configured to hold a sample tube and one or more optical devices configured to receive an image of a barcode on the sample tube. A reflective surface of the tube holder is configured to reflect the image of the barcode to the one or more optical devices when the tube is placed in the tube holder in an orientation such that the barcode is not in a direct line of sight of the optical device.

According to one aspect of some embodiments, the reflective surface includes a conical shaped internal surface of the tube holder or a substantially parabolic shaped internal surface of the tube holder. According to another aspect of some embodiments, the optical devices include one or more lenses and/or imaging sensors or may also include a light source and a photodetector. According to a further aspect of some embodiments, a carrier may include a processor configured to receive barcode information from the one or more optical devices when the tube is inserted in the tube holder or when in response to a request.

According to another embodiment of the invention, a carrier for use in an in vitro diagnostics environment includes a tube holder configured to hold a sample tube and a plurality of optical devices configured to receive an image of a barcode on the sample tube. The plurality of optical devices is arranged on a surface of the tube holder such that the barcode is in the line of sight of at least a portion of the plurality of optical devices.

According to another aspect of some embodiments, the surface of the tube holder includes an internal surface, and the tube holder is configured to accept a tube such that the barcode is substantially within the tube holder. According to another aspect of some embodiments, the surface of the tube holder comprises an external surface, and the tube holder is configured to accept a tube such that the barcode is substantially outside the tube holder.

According to another embodiment of the invention, a carrier for use in an in vitro diagnostics environment includes a tube holder configured to hold a sample tube, one or more optical devices configured to receive an image of a barcode on the sample tube and a rotation device configured to rotate the sample tube to orient the barcode within a line of sight of at least one of the one or more optical devices.

According to another aspect of some embodiments, the rotation device comprises a gear, an externally applied friction wheel, or a motor. According to another aspect, the optical devices include one or more lenses and/or one or more imaging sensors.

According to another embodiment of the invention, a rack transporting samples in an in vitro diagnostics environment includes a plurality of tube holders, each configured to hold a sample tube and a plurality of optical paths within the structure of the rack for conveying images of each sample tube to one or more optical ports. The optical ports are suitable for observing barcode information associated with tubes placed in the plurality of tube holders.

According to another aspect of some embodiments the optical paths comprise one or more optical fibers.

According to yet another embodiment of the invention, a rack transporting samples in an in vitro diagnostics environment includes a plurality of tube holders, each configured to hold a sample tube, a plurality of optical devices on one or more surfaces within the rack for observing barcodes of each sample tube, and an electrical port coupled to the plurality of optical devices for communicating images of the barcodes between the optical devices and the electrical port.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 4A is a perspective view of an exemplary carrier that can be used with the embodiments disclosed herein;

FIG. 5 is a system block diagram of the control systems including onboard active carriers that can be used with certain embodiments disclosed herein;

FIG. 12 is a perspective view of an array of exemplary tube holders for use with some embodiments disclosed herein;

FIG. 13 is a perspective view of an array of exemplary tube holders for use with some embodiments disclosed herein;

DETAILED DESCRIPTION OF ILLUSTRATIVE EMBODIMENTS

Figure 1:
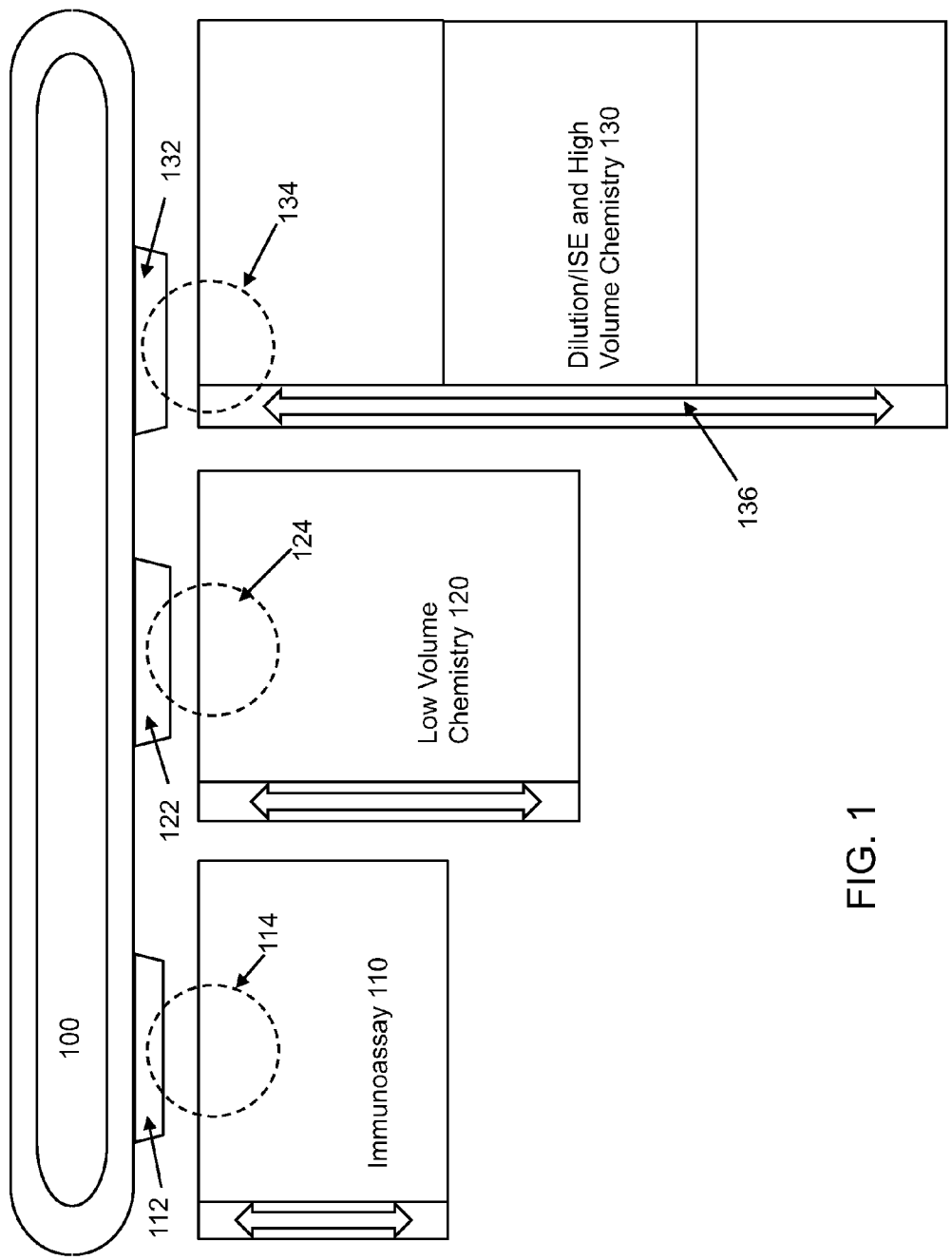
FIG. 1 is a top view of an exemplary clinical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each mModule can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

The above problems in the prior art have motivated the discovery of improved apparatus and methods for reading barcode information of tubes already placed in carriers, or racks. Specifically, carriers and/or racks can include optical means that allow the detection and observation of barcode information on the side of sample tubes in situ. This can reduce the need for removing samples from carriers or racks for purposes of identification. This can reduce chain of custody issues and sample contamination, as operator involvement can be reduced as samples are handled and transported throughout an IVD system. This can also reduce handling of sample tubes by automation as well.

In some embodiments, the carriers that transport fluid samples are active devices. These can include semiautonomous robots that include onboard power and memory. The memory can include, inter alia, the current status of the sample to be displayed, while the power can be used to update the rewritable surface to display that status. In some embodiments, the optical means disclosed herein are applied to carriers, portions of carriers, and/or racks for transporting tubes. As discussed herein, the optical devices used with embodiments of the present invention can be passive, and can therefore be used with active or passive carriers or racks. In some embodiments, optical devices used with carriers or racks can include active devices, such as cameras. In these embodiments, the carriers or racks can be active devices. In some embodiments, active devices such as cameras are used with normally passive racks or carriers, which can provide means for providing temporary power to active devices.

In some embodiments, active carriers can be used to transport samples substantially faster than prior methods, allowing reliable scheduling of tests, a reduction of traffic in the automation system, and reduced latency and reliable throughput of tests within the analyzer. Some embodiments exploit the semi-autonomy of the sample carriers to provide transit between stations in less than a single operation cycle, effectively removing or greatly reducing automation of sample placement as a performance bottleneck, and allowing more flexible sample scheduling options.

Embodiments of the present invention may include systems and methods that provide a more efficient lab automation system to allow samples to be shuttled between and amongst various analyzer testing stations with less latency and more individual control. Embodiments of the present invention can reduce or eliminate queues experienced by samples traversing the automation system. Usually, samples need to undergo many different types of testing in an automated clinical analyzer (analyzer), which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

In some embodiments, multiple analyzers can be used in the same IVD environment. For example, older analyzers, standalone analyzers, or analyzers that provide substantially different testing mechanisms can be on separate automation systems. An operator may carry trays of samples between and amongst these machines.

Modular Automation System for Use with Carriers

An exemplary track geometry, for use in transporting samples within an analyzer typical in prior art configurations, is shown in FIG. 1. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within the IVD environment, such as fluid samples, reagents, or waste. Fluids, such as patient samples, can be placed in a container or vessel, such as a test tube, vial, cuvette, etc. that can be transported by a carrier. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
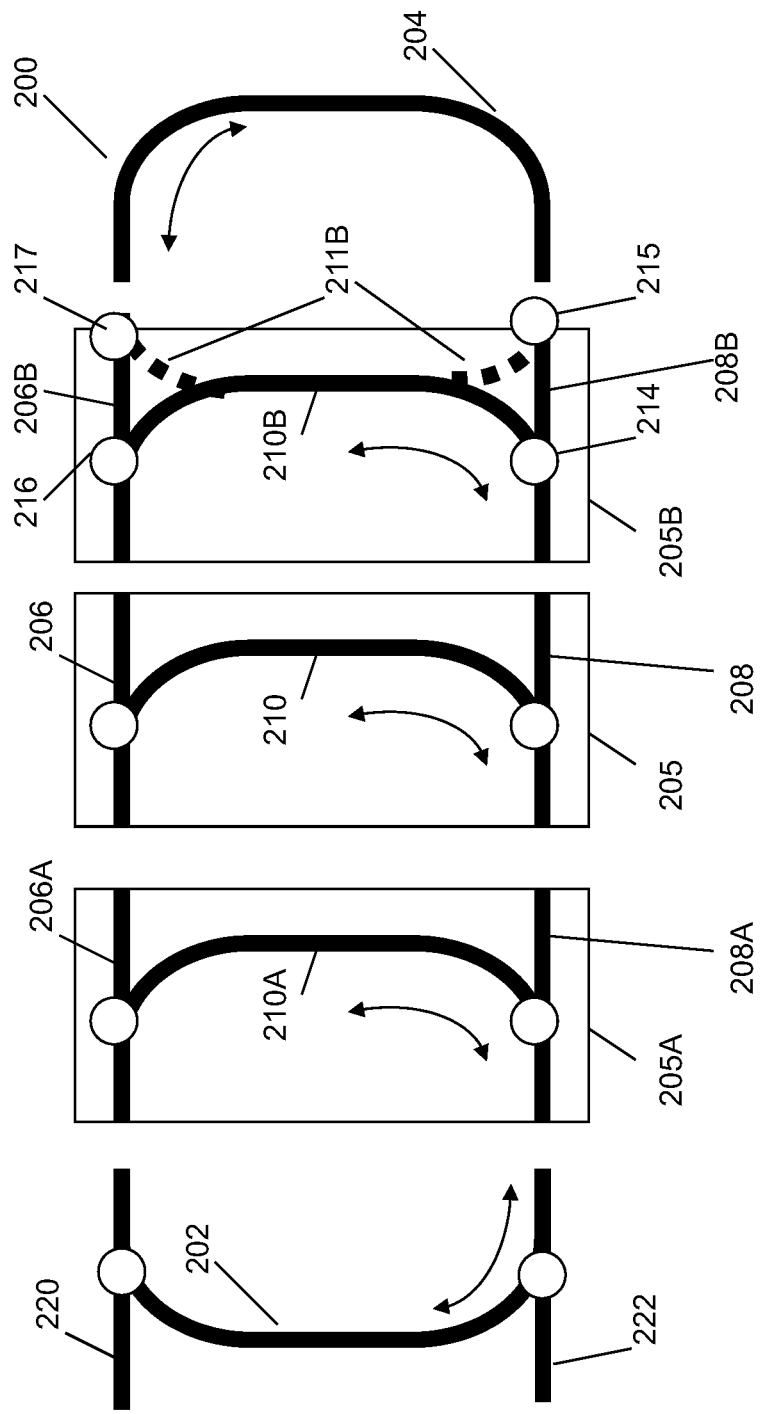
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems. With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
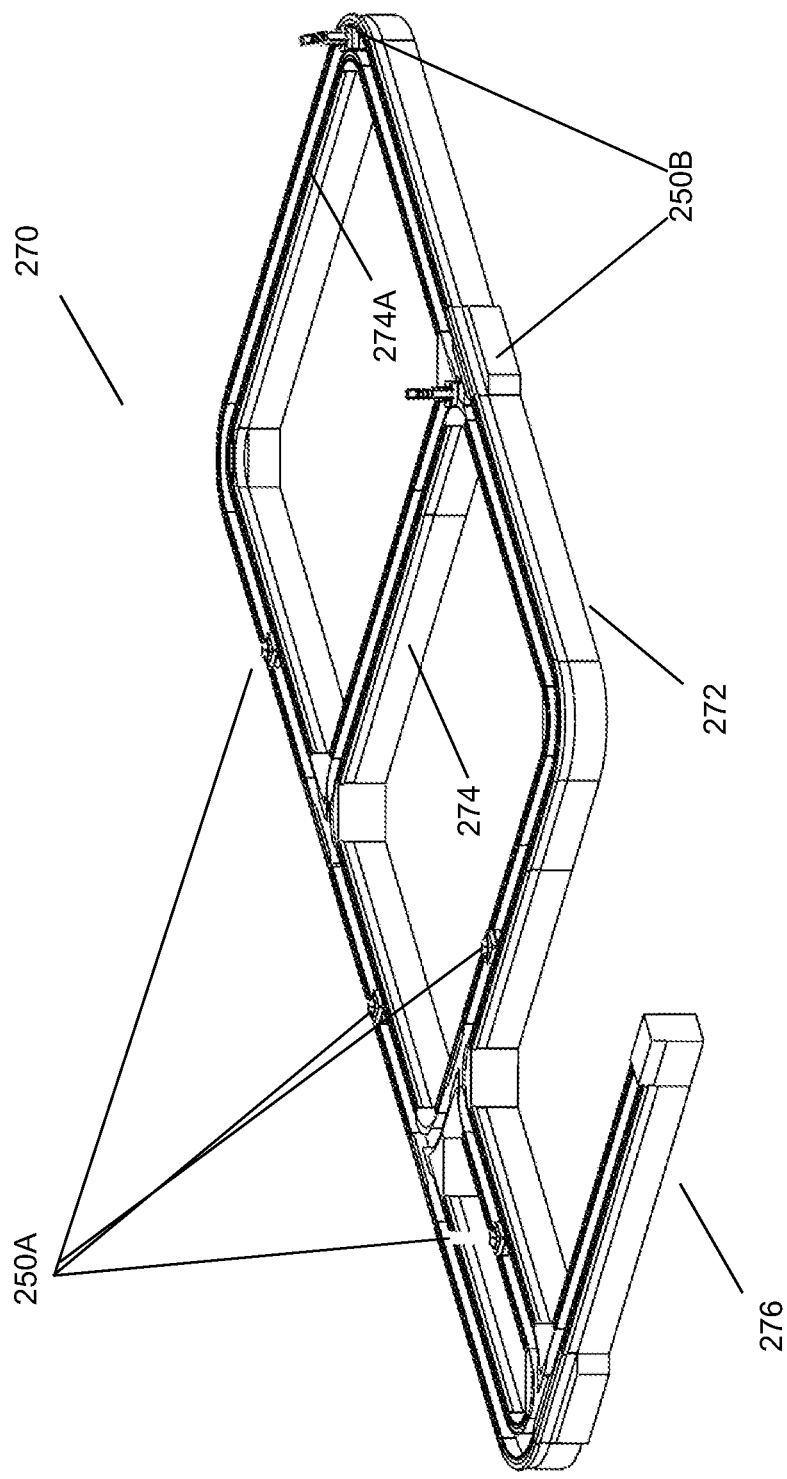
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
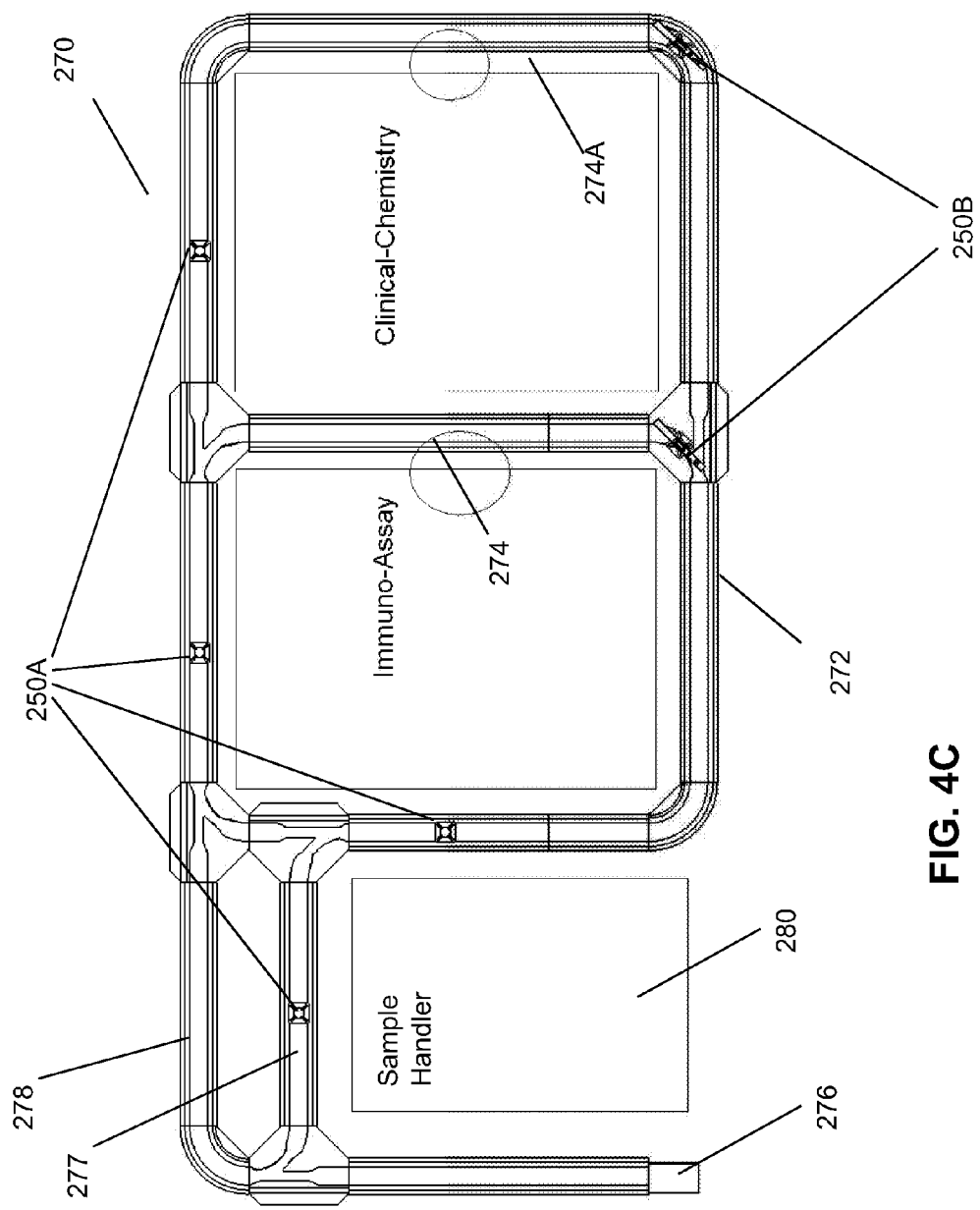
FIG. 4C is a top view of an exemplary automation systems carrier that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Some embodiments of the present invention can utilize intelligent carriers to enable certain improvements over passive pucks on the friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has a prior knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although, in some embodiments, a central controller sends routing instructions to the carrier to be carried out). For example, position encoding or markers in the track can be read by the carrier to determine a carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

FIG. 5 shows a top-level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 315 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Barcode Reading

In some embodiments of the carriers described herein, the carrier is outfitted with a single slot or multiple slots, wherein each slot may be configured to hold a fluid container, such as a tube. These slots may be referred to as tube holders. A multi-slot carrier may act as a rack or a single carrier within the automation system. For example, a rack carrier may refer a tray in embodiments when the multi-slot carrier does not travel along an automation track (i.e., carried by an operator or when not configured to be a carrier within an automation system, such as two-dimensional racks that are used to store a plurality of samples for later use or easier manual carrying and storage). Embodiments of the present invention may be suitable for use with any of these configurations.

As described in FIG. 5, carrier 300 can include a barcode reader 314. Barcode reader 314 can include optical devices, such as lenses or fiber-optic cables, for conveying images of the barcode to other optical devices, such as fiber-optic cables or cameras. In some embodiments, carrier 300 includes passive optics and an active imaging device, such as a CCD camera or CMOS digital imaging sensor. In some embodiments, the optical devices are integrated camera units, like those used in cell phones, which can be employed at little cost due to the ubiquity of their use in other electronic devices. These cameras can be used in an array or individually. In some embodiments, carrier 300 does not include onboard active imaging components, but rather uses passive components to provide one or more optical paths to allow an external camera viewing the surface of carrier 300 to observe the barcode information of tubes being transported by the carrier. Similarly, racks, which may include passive racks (e.g., storage trays or passive carriers), can include similar optical means to allow an optical path between the barcode of one or more tubes contained in the rack and an observable surface of the rack. This can allow a rack to be moved in front of a camera and barcode information for a plurality of tubes to be observed simultaneously or in rapid succession. Furthermore, racks may include one or more onboard active imaging devices, such as CCD or CMOS image sensors (e.g., cameras), to allow a rack to read barcode information from one or more tubes stored in the rack.

In some embodiments, a tube must be oriented in a certain direction when it is observed, within a certain tolerance, to allow line of sight access to the barcode on the tube. As described herein, some embodiments of tube holders include mechanisms to allow for the rotation of a tube automatically. In these embodiments, the orientation of the tube when it is inserted into the tube holder can be in any angular direction in the horizontal plane. The mechanism will adjust/correct the orientation. In some embodiments, the visual feedback can be provided to a user via the tube holder. For example, a light or other visual indicator can be turned on when a camera detects a barcode. In other embodiments, audio feedback may be used, such as a beep. This can allow a simple arrangement that requires a single optical device to have line of sight access to a barcode, but can also increase accuracy by ensuring that a user has oriented a tube properly. In some embodiments, a vessel can be shaped in shapes other than round. For non-round vessels, a vessel holder (i.e., a tube holder not limited to holding tubes) can have a recess shaped to ensure that a vessel can only be placed in a vessel holder when oriented properly. Accordingly, in some embodiments, the tube holder can include non-tubular vessel holders.

In some embodiments, a plurality of optical devices may be used to compensate for the orientation of a tube placed in a tube holder. For example, multiple optical devices can be provided in a tube holder such that more than one line of sight is available for viewing a barcode. In some embodiments, multiple lenses can be provided in a tube holder to provide multiple optical inputs for viewing a tube. In some embodiments, multiple image sensors are placed in the receiving portion of the tube holder to allow viewing of a barcode at multiple points in the tube holder. The arrangement can include 3 to 8 or more imaging devices in an array, such as a one-dimensional array that surrounds the tube in a ring-like fashion. Accordingly, a substantial portion of the barcode can be read regardless of the initial orientation of the sample tube when it is placed in the tube holder.

In some embodiments, the configuration of the tube holder includes reflective or refractive elements that allow for greater tolerance of the orientation of the barcode, or allow any orientation of the barcode, and still facilitate successful reading of the barcode even when the barcode is not otherwise viewable in a direct line of sight of an imaging device. In these embodiments, optics can be used to compensate for the initial orientation of the barcode when it is inserted into the tube holder. That is, regardless of the initial angular orientation of the tube in the horizontal plane, when it is inserted into the holder, the reflective (or refractive) surfaces in the tube holder can reflect (or refract) a sufficient portion of an image of the barcode to allow the barcode to be read. In some embodiments, a tube holder includes one or more reflective surfaces (i.e., mirror surfaces) that allow images of a barcode to be redirected to one or more optical devices for observation. In some embodiments, a tube holder includes one or more refractive surfaces, like a prism or lens, that allows images of a barcode to be redirected to one or more optical devices. In some embodiments, the range of allowable orientations of the tube is greatly increased versus line-of-sight measurements. In some embodiments, the range of allowable orientations of the tube is increased to allow any orientation of initial placement of the tube into the holder.

In some embodiments, a tube holder is configured to include at least a substantial portion of a barcode within the receiving portion of the tube holder, such as, for example, 90% or more of the barcode. In these embodiments, optical devices capable of viewing inside the receiving portion may be used to observe the barcode.

In other embodiments, a tube holder can be configured such that a substantial portion of a barcode protrudes outside of the receiving portion of the tube holder. In these embodiments, optical devices can be used that do not necessarily have a line of sight view into the receiving portion of the tube holder. For example, one or more optical devices can be placed on a top surface of a carrier with line of sight access to an area above the top of the tube holder. When a tube is oriented to provide line of sight access between that optical device and a barcode protruding from the tube holder, the barcode can be read.

The embodiments disclosed herein are not intended to be limited to configurations where the barcode is only viewable within the receiving portion of the tube holder. Furthermore, in some embodiments, a tube holder can be optically transparent, such as being made of clear plastic. In these embodiments, optical devices can be placed external to a tube holder and serve substantially the same function as embodiments described herein.

Figure 6A:
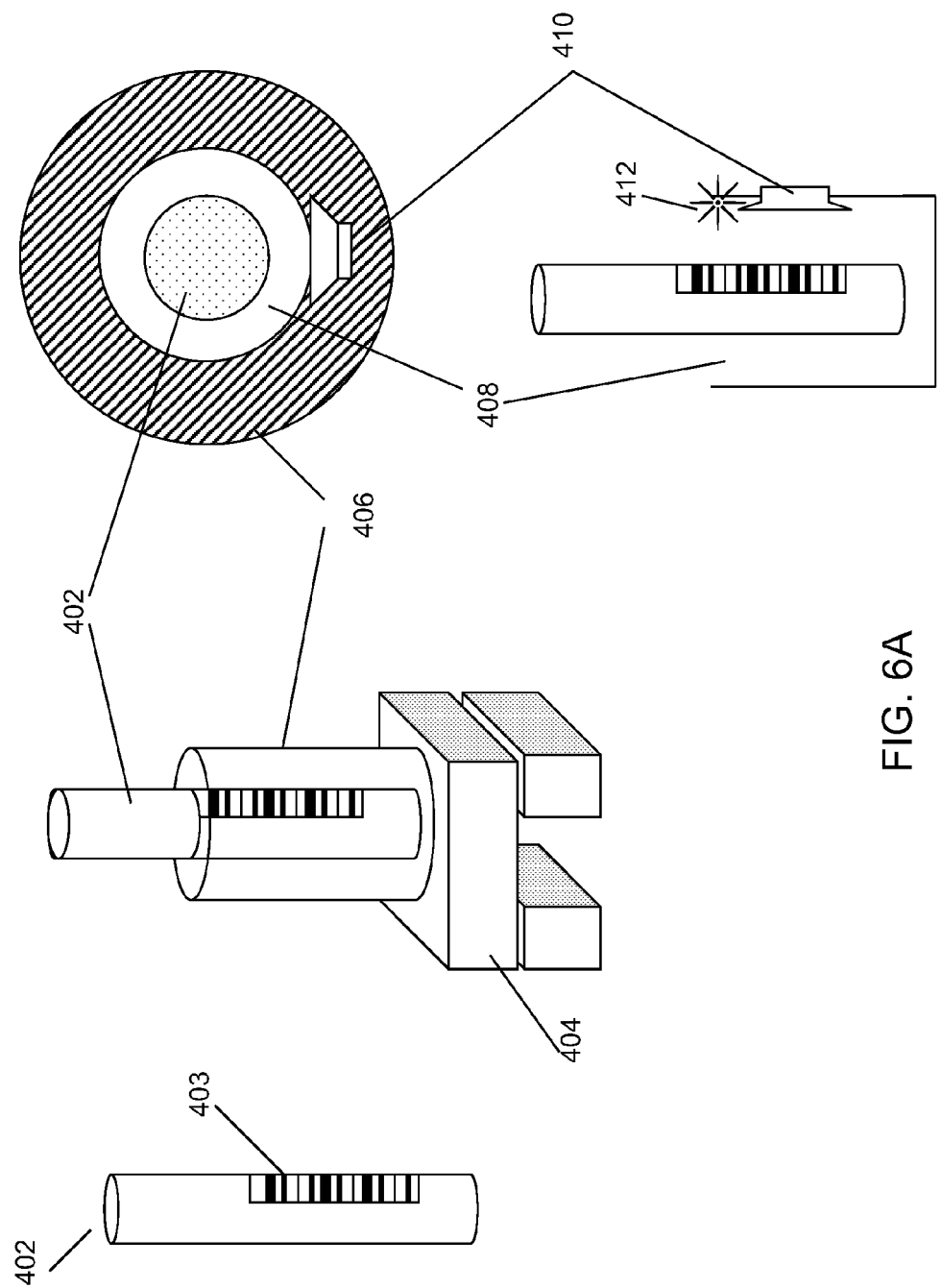
FIG. 6A is a diagrammatic view showing a perspective view, a top view, and a cross sectional view of an exemplary tube holder for use with some embodiments disclosed herein.

FIG. 6A shows an exemplary carrier 404 for holding a tube 402 having a barcode 403 in multiple views. In this embodiment, the tube 402 is placed in a tube holder 406 having a receiving portion 408. Receiving portion 408 can include a hole, receptacle, or recess for receiving tube 402. In some embodiments, tube holder 406 can include mechanical mechanisms for holding tube 402 securely. This can include latches, levers, spring mechanisms, friction fits, or the like. In this embodiment, an optical device 410 is placed in this structure of holder 406. As shown, the optical device 410 can be placed in a vertical wall such that optical device 410 can observe barcode 403 when tube 402 is properly oriented. In some embodiments, a light source 412, such as a laser, light bulb, LED, or the like, is also placed in holder 406. Light source 412 can be used to illuminate the markings in the barcode for observation by optical device 410.

Optical device 410 can include passive optics, such as a lens, lenses, fiber-optic cables, or the like. In some embodiments, optical device 410 can further include an image sensor, such as a CCD or CMOS sensor (e.g., a camera). In some embodiments, fiber-optic arrays can be used to observe the image presented to device 410, and provide an optical path to an active image sensor elsewhere. In these embodiments, the image sensor can be onboard carrier 404, or may be off carrier 404. In embodiments in which optical device 410 does not include an active sensor, an optical port, such as a fiber-optic window in a surface of the carrier, can be provided for conveyance of barcode information to an external imaging device, such as a camera. It should therefore be appreciated that optical devices described herein can include passive optics and/or active optics, such as imaging devices.

Figure 6B:
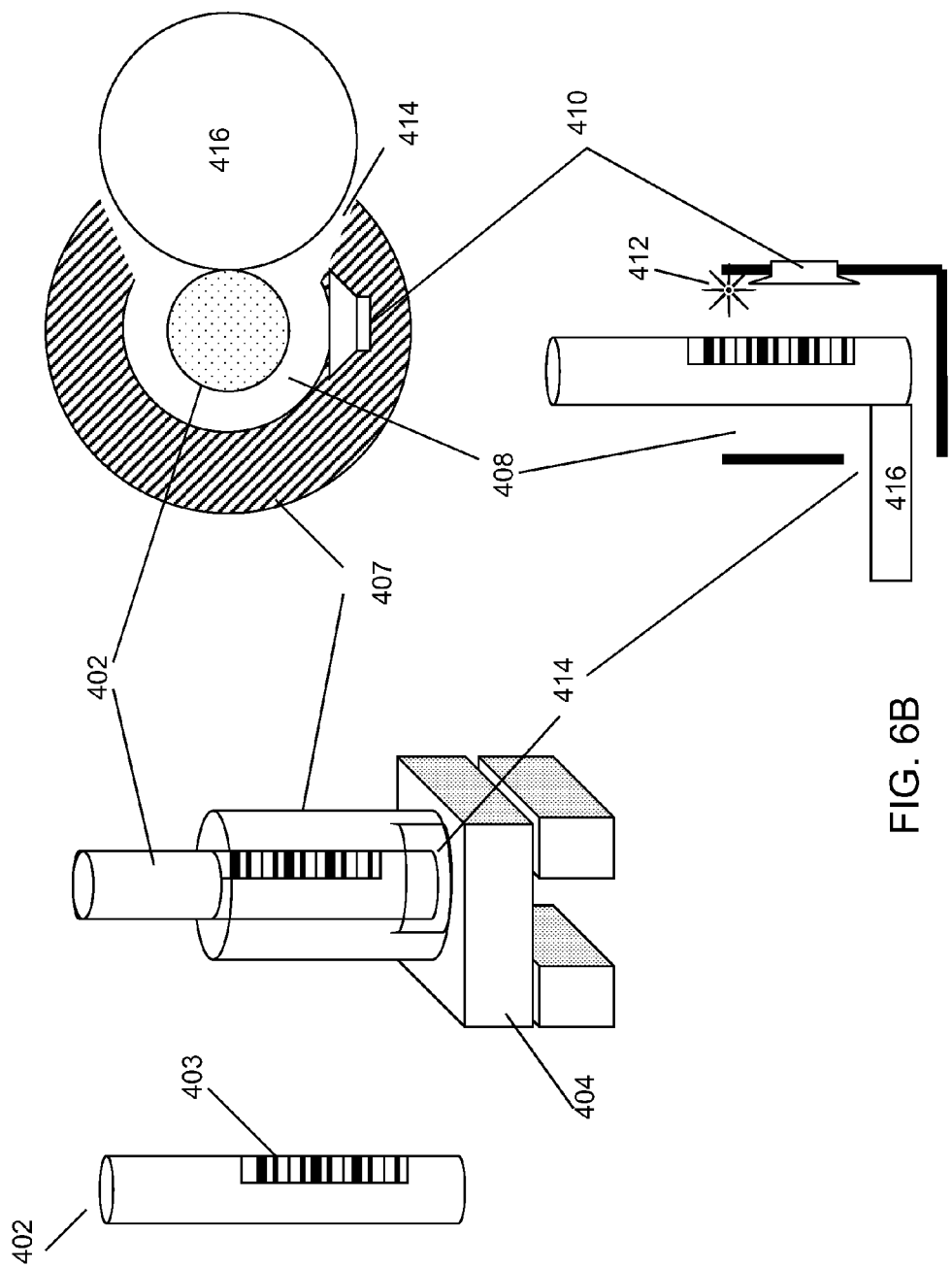
FIG. 6B is a diagrammatic view showing a perspective view, a top view, and a cross sectional view of an exemplary tube holder for use with some embodiments disclosed herein.

FIG. 6B shows a similar carrier 404 for holding a tube 402 having a barcode 403. In this embodiment, tube holder 407 includes an opening 414. As described with respect to FIG. 6A, optical device 410 requires a direct line of sight to the barcode 403. Accordingly, tube 402 should be properly oriented such that barcode 403 faces optical device 410. By providing an opening at 414 in the structure of holder 407, an external device can rotate tube 402 within receiving portion 408. For example, a rotation device, such as a friction wheel 416 can be temporarily engaged with tube 402 to rotate tube 402. Friction wheel 416 may be provided onboard the carrier 404, or may be provided temporarily by a station within the automation system. For example, prior to moving carrier 404 onto an automation system track, a station may rotate tube 402 with a friction wheel 416 to provide line of sight access between optical device 410 and barcode 403.

Figure 7:
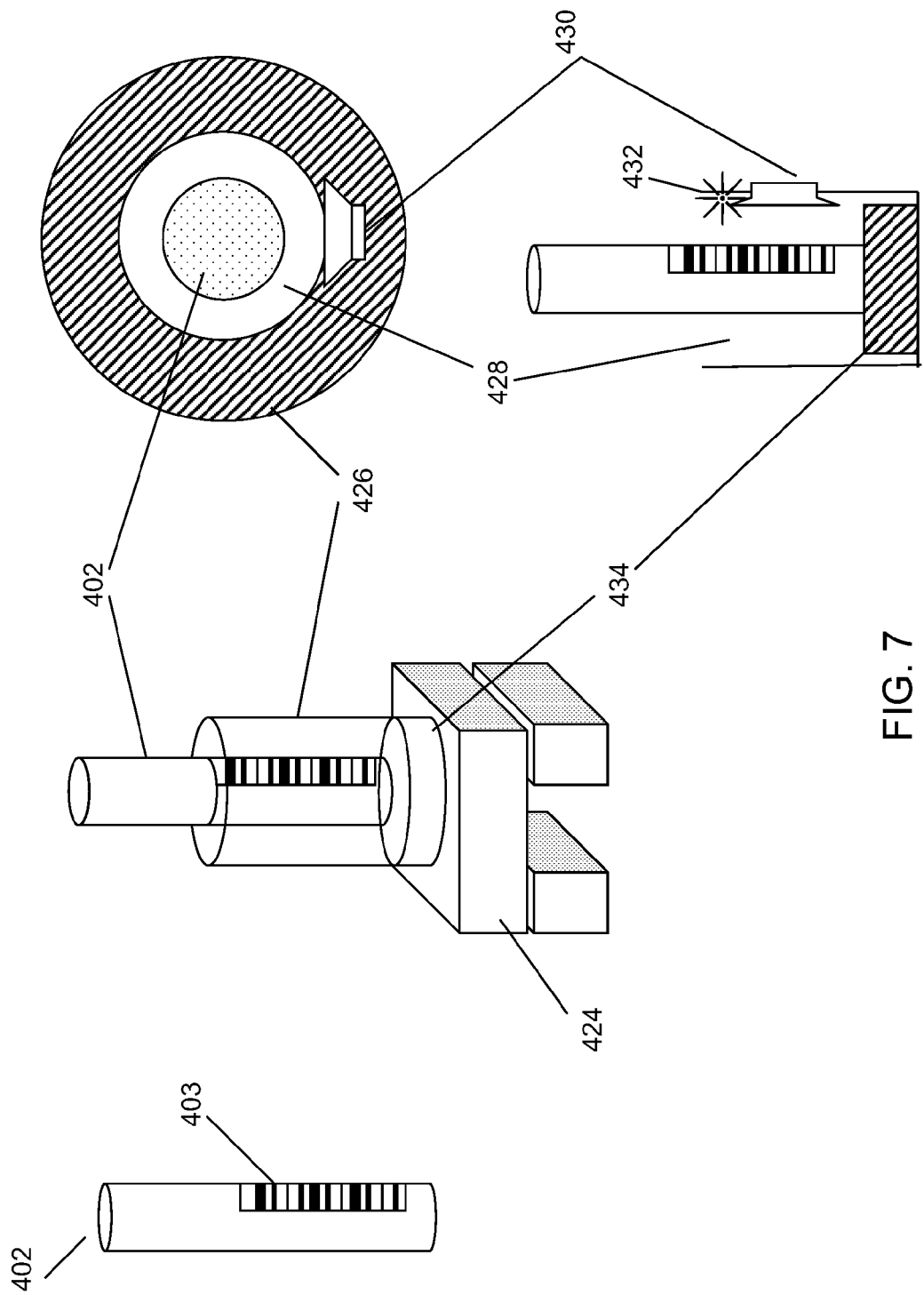
FIG. 7 is a diagrammatic view showing a perspective view, a top view, and a cross sectional view of an exemplary tube holder for use with some embodiments disclosed herein.

FIG. 7 shows another embodiment of a carrier 424 that can rotate a tube 402 within a tube holder 426, to orient barcode 403 for observation by an imaging device 430. As discussed with respect to other embodiments, tube 402 may be placed in receiving portion 428 within tube holder 426. A rotation device 434 may be provided as part of the carrier 424. Rotation device 434 may be a motor or gear for engaging with a motor or gears. Rotation device 434 can be used to rotate tube 402 to provide line of sight access between optical device 430 and barcode 403. In some embodiments, light source 432 can be used to illuminate barcode 403 for observation.

Figure 8:
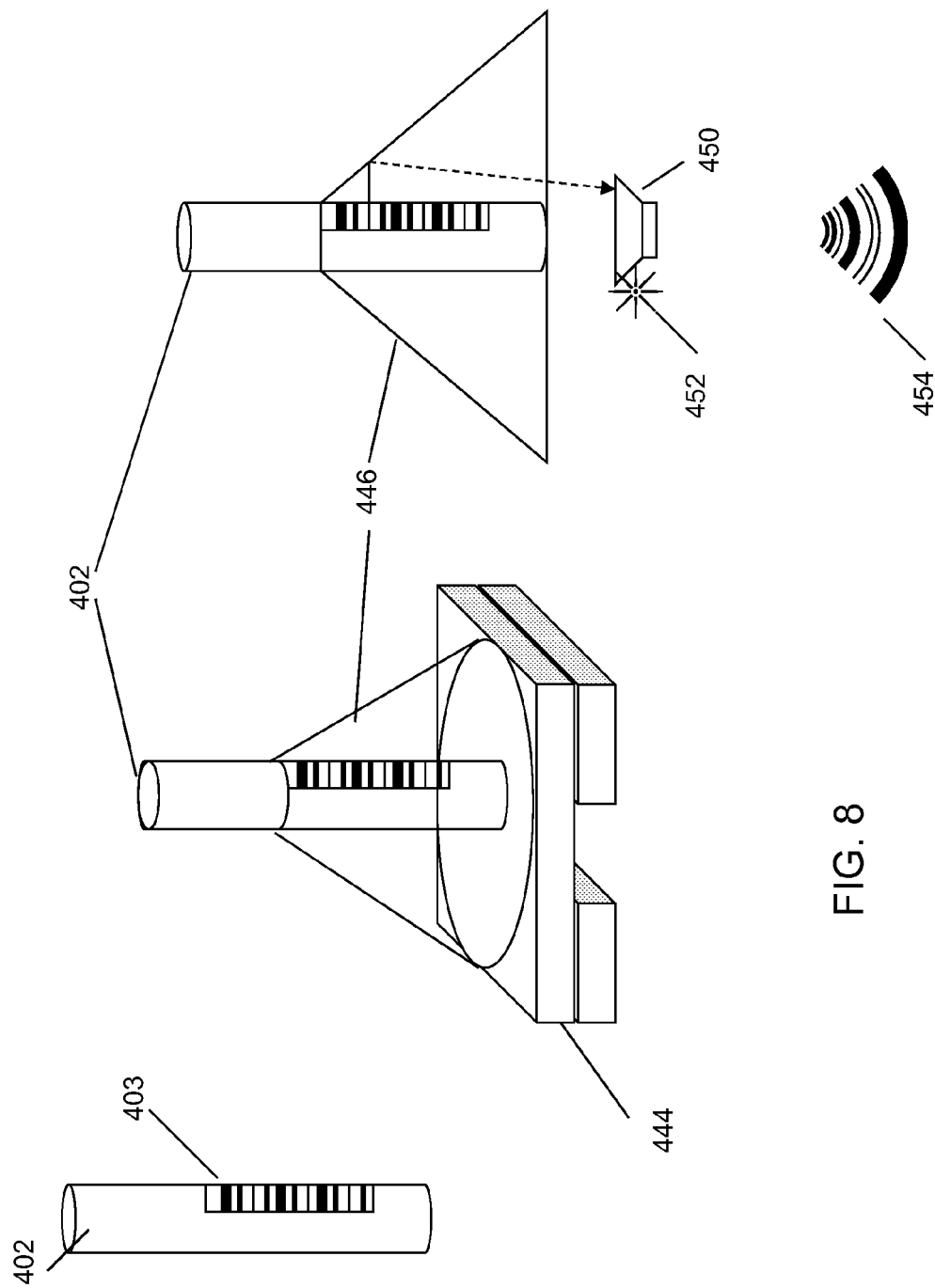
FIG. 8 is a diagrammatic view showing a perspective view, a cross sectional view, and a sample image result of an exemplary tube holder for use with some embodiments disclosed herein.

Reflective surfaces can be used to allow observation of a barcode without direct line of sight between the observing optical device and the barcode. FIG. 8 shows an embodiment of a carrier 444 having a tube holder 446 for holding a tube 402 with a barcode 403. In this embodiment, the internal surface of the tube holder 446 includes reflective non-vertical inner sidewalls. In this example the sidewalls of tube holder 446 are conical. Because the internal surface of tube holder 446 is conical, it provides a concave optical surface that can reflect light to an optical device 450 placed underneath a tube 402.

In some embodiments, the internal surface of tube holder 446 is made of a reflective material, such as polished metal or other mirrored surfaces as known in the art. The internal surface is effectively a conical mirror. This reflective surface can also include a semi-reflective surface, such as a polished surface of an opaque, translucent, or transparent material. In some embodiments, light source 452 can be used to illuminate barcode 403 using the reflective surface of tube holder 446. Because the surface of tube holder 446 is conical, the angular rotation of the tube 402 within tube holder 446 can be in a broad range of orientations and still allow optical device 450 to observe barcode information. In some embodiments, the conical shape of tube holder 446 allows for barcode reading when tube 402 is in any orientation.

Image 454 is an example of an observed image by optical device 450, when observing the reflections off of the internal surface of tube holder 446. Pattern 454 may include curved portions rather than straight lines due to the curved nature of the conical surface of tube holder 446. When observed by an image sensor, this image can be converted to Cartesian coordinates to recover the original barcode having straight lines. In some embodiments, this translation will be done before decoding the barcode. In other embodiments, a processor decoding the observed barcode will use other image processing techniques to detect the barcode information without converting the image to Cartesian coordinates. For example, a line can be chosen in the image and light and dark areas along that line can be used to determine the barcode pattern.

In some embodiments, the internal surface of tube holder 446 can include other shapes. For example, an elliptical cone can be used. In some embodiments, vertically concaved or convex surfaces, such as domes or cone-shaped surfaces, can be used. In some embodiments, the internal surface of the tube holder 446 is a substantially parabolic reflector. The substantially parabolic reflector may include a single continuously curved reflector/mirror or a plurality of substantially flat reflective surfaces arranged to for a substantially curved overall surface, or any combination thereof. It is further contemplated that curved surfaces having a curve similar to a parabola (such as hyperbolic surfaces) that allows similar multi-angle viewing may also be used to achieve substantially the same result as embodiments described herein.

Figure 9:
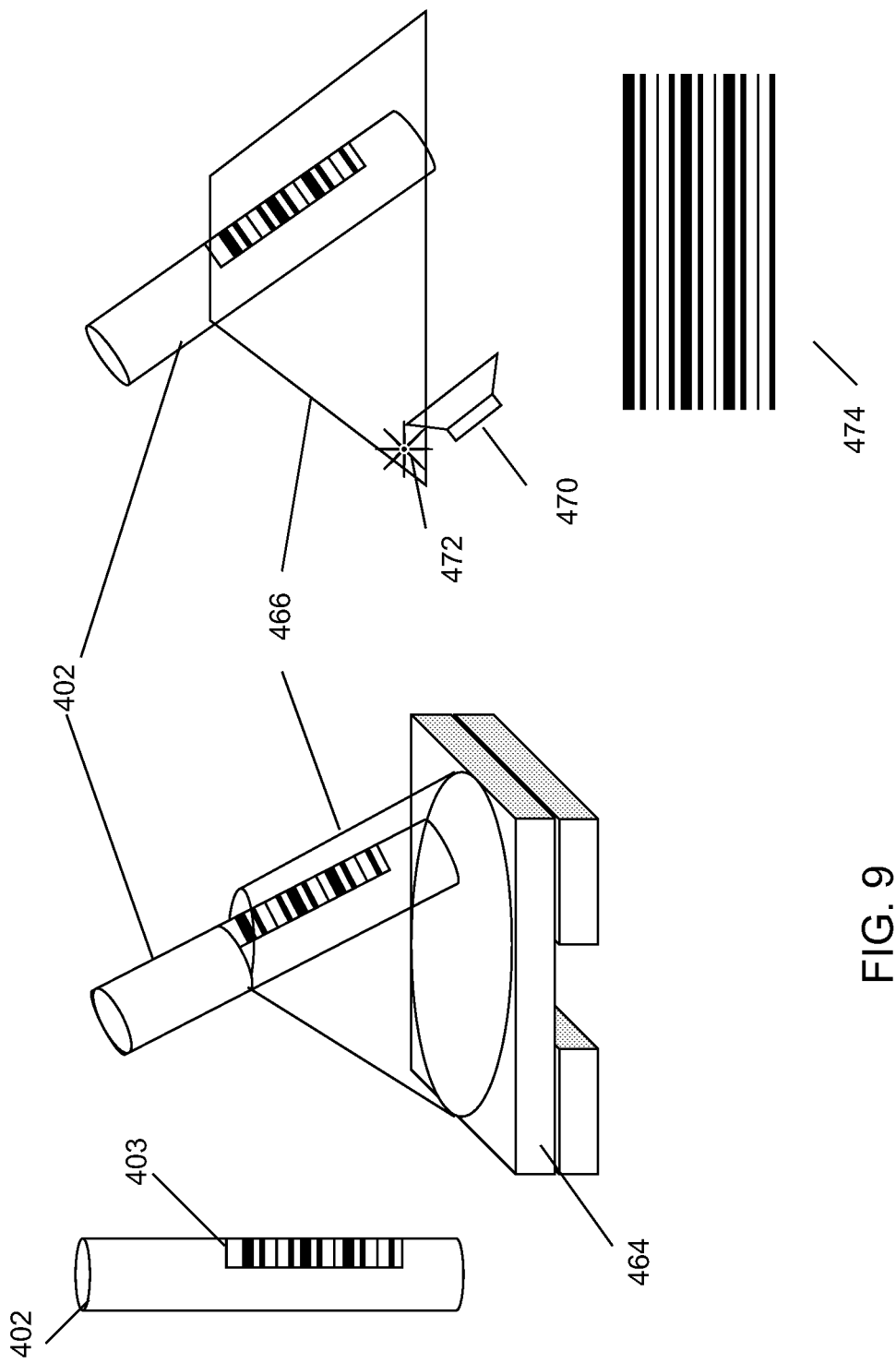
FIG. 9 is a diagrammatic view showing a perspective view, a cross sectional view, and a sample image result of an exemplary tube holder for use with some embodiments disclosed herein.

FIG. 9 shows another embodiment of a carrier 464 for holding tube 402, having a barcode 403. Tube holder 466, has an internal reflective surface and a conical shape. Tube 402 can be placed in a vertically tilted orientation. This allows the internal surface of the tube holder 466, to act as a parabolic surface. In effect, the internal surface of tube holder 466 provides a parabolic mirror to reflect barcode information to optical device 470, without requiring a direct line of sight. Light source 472 may be used to illuminate the barcode 403 for observation. Pattern 474 shows an exemplary image result for a barcode. In some embodiments, the image result may have slight bowing due to the straight walls of the conical surface of the holder 466 for a lens that is substantially smaller than the size of the barcode 403. Using the conical surface of tube holder 466, tube 402 can be placed in virtually any orientation and barcode 403 can be properly observed by optical device 470.

Figure 10:
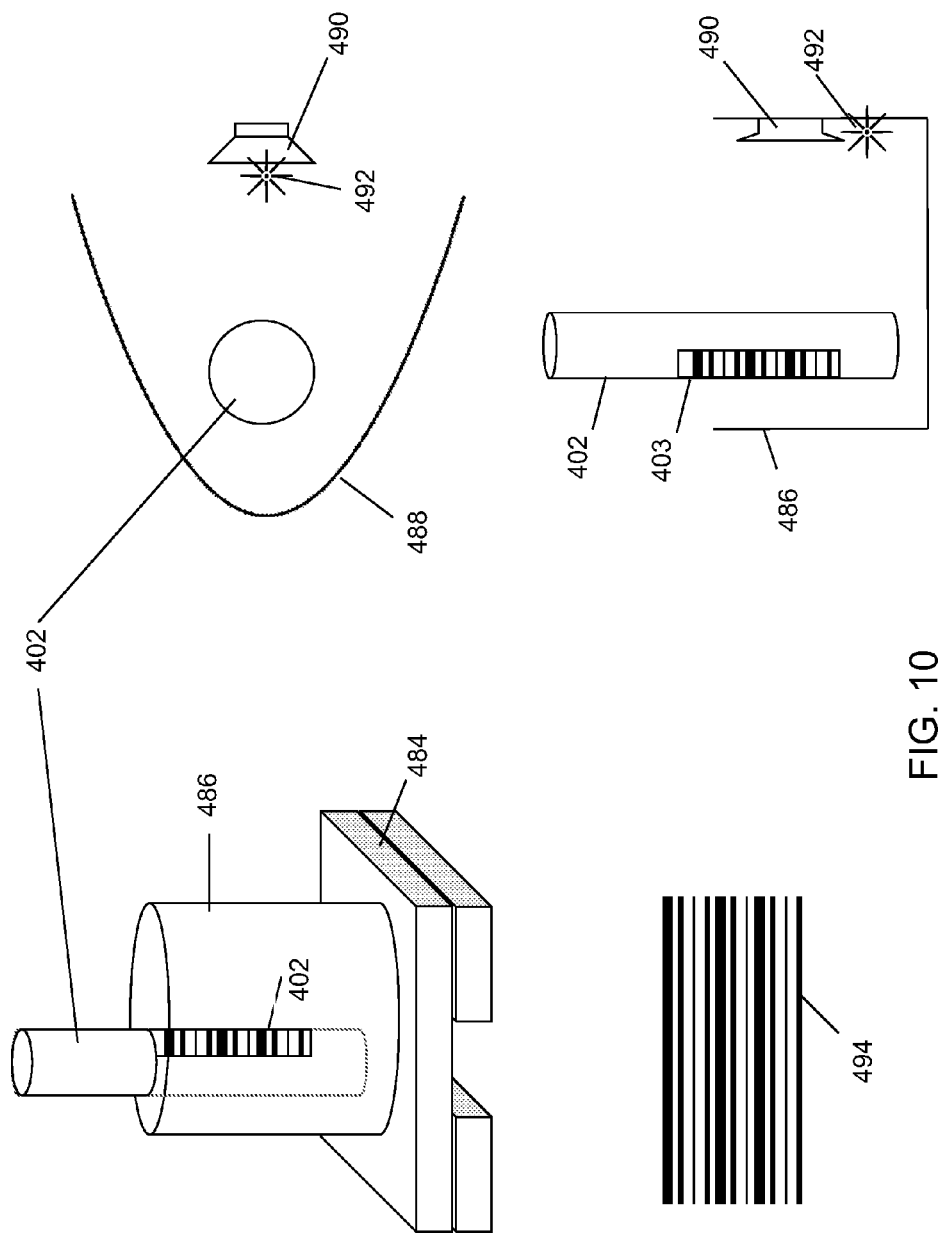
FIG. 10 is a diagrammatic view showing a perspective view, a top view, a cross sectional view, and a sample image result of an exemplary tube holder for use with some embodiments disclosed herein.

FIG. 10 shows another embodiment of a carrier 484 having a tube holder 486 for holding tube 402. The internal surface 488 of tube holder 486 can have a parabolic profile and can be reflective (i.e., at least partially reflective). In this embodiment, internal surface 488 has substantially vertical sidewalls and is substantially parabolic in the horizontal direction. Tube 402 can be placed at the focal point of the parabolic mirror formed by the sidewalls of internal surface 488. Optical device 490 can be placed on an opposite wall from the parabolic surface. The image of the barcode 403 can reflect off curved surface 488 to be observed by optical device 490. Light source 492 can illuminate the scene. In some embodiments, light source 492 is coextensive in the horizontal plane with optical device 490. Pattern 494 shows an exemplary image observed by optical device 490. Using the parabolic surface 488, tube 402 can be placed in virtually any rotational orientation and barcode 403 can be properly observed by optical device 490.

Because barcodes include marks that have some width, tubes can be placed in tube holders having reflective surfaces with a fair degree of tolerance, in some embodiments. Furthermore, curved or conical shapes can include other shapes, such as spherical or elliptical shapes, or curves comprising geometric planar surfaces, while allowing successful reading of barcode information.

Figure 11:
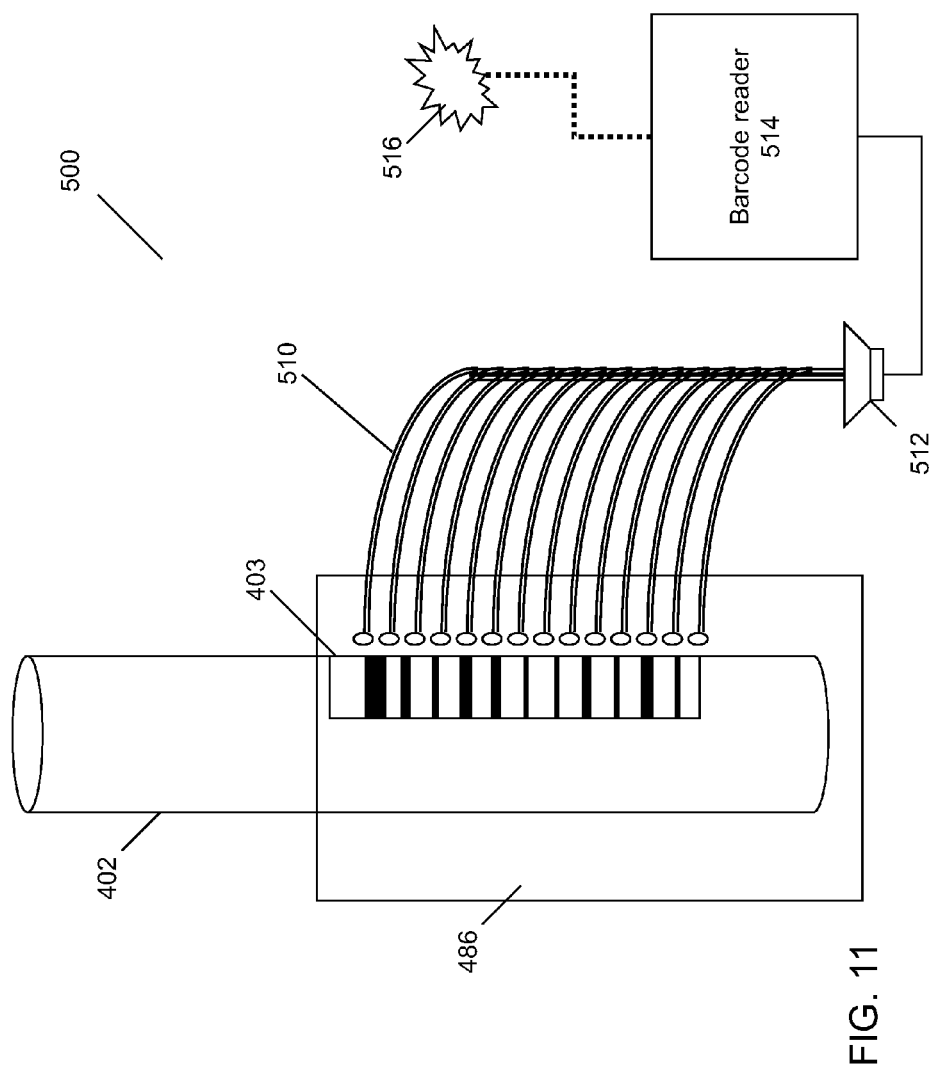
FIG. 11 is a diagrammatic view of an exemplary tube holder and barcode reading system for use with some embodiments disclosed herein.

FIG. 11 shows a barcode reading system 500 that can be used with many of the structural embodiments disclosed herein. The optical device that observes barcode 403 on tube 402 can be composed of one or more fiber-optic bundles. In the example shown in FIG. 11, fiber-optic bundle 510 includes a plurality of fiber-optic fibers, which can also include lens structures at the tip of each fiber. In some embodiments, lens structures are not used if the tips of fibers are placed in close proximity to a barcode. In this example, the fibers in bundle 510 are spaced in a predefined pattern suitable to observe a substantial portion (or all) of barcode 403. The example of FIG. 11 shows fibers 510 only on one side of the tube holder. However, it will be appreciated that any arrangement of fibers may be suitable for use with the tube holder. For example, individual fibers can be spaced around the surface of the receiving portion of the tube holder 486. In this manner, the arrangement of fibers can be used to allow a broad range of orientations, such as 90 degrees or 360 degrees, while still allowing successful reading of a barcode 403.

Fiber optic bundle 510 can provide an array of fiber-optic signals to an image sensor 512. Image sensor 512 can include any conventional image sensor, such as a CCD or CMOS image sensor. Image sensor 512 provides an electrical signal to barcode reader 514, which can include circuitry, such as a processor, for decoding the barcode 403 from the image signal. In some embodiments, barcode reader 514 is part of the onboard processing system for a carrier, and includes a processor, memory, and processing instructions. Barcode reader 514 can also be used to provide an alert 516 to a user. For example, alert 516 may be an audio alert or visual alert to a user to indicate that barcode reader 514 has captured the barcode. In embodiments in which the orientation of tube 402 is important for reading the barcode (or any other purpose), this can be used to indicate to the user that tube 402 is operably oriented. In some embodiments, fiber optic bundle 510 and image sensor 512 can be replaced with an array of image sensors mounted inside tube holder 486 with a line of sight to the barcode 403, in much the same way as the lenses of bundle 510.

It should be appreciated that image capture and image processing may be accomplished by the same or separate circuits. In some embodiments, the barcode information may be processed separate from the carrier. For example, the barcode information may be captured as an image or as a sensor signal from one or more photodetectors. This captured information can be sent to a processing circuit, such as a DSP or CPU. The processing circuit may be part of a separate device (e.g., central controller, one or more sub-controllers, and the like) from that device capturing the barcode information (e.g., an image sensor and onboard processing circuits of a carrier or reading station) and processed by the separate device. This can allow lower powered processors onboard the carrier. The barcodes may be processed by one or more processors, or dedicated decoding circuits. Similarly, barcodes may be entirely read and decoded locally, allowing carriers to decode barcodes rapidly with limited communication overhead.

The optical structures disclosed herein can be used for trays (e.g., non-carrier racks), as well as carriers. FIG. 12 shows a rack 520, which includes a one-dimensional array of individual tube holders, such as 522. In some embodiments, each tube holder 522 includes its own image sensor. The embodiment shown in FIG. 12 includes an optical port 524 that allows for observation of barcode information via an external image sensor 526. Optical port 524 can include the output of a plurality of optical guides, such as fiber optic bundles or other internal reflective devices. The input to these optical guides can be the optical devices described with reference to previously-described embodiments. In this example, image sensor 526 can simultaneously or sequentially observe the individual outputs of optical port 524 to read the barcodes of one or more tubes in rack 520.

FIG. 13 shows an alternate embodiment of the rack 520. As shown in FIG. 13, rack 530 can include an array of tube holders, such as 532. Each tube holder in rack 530 can include an image sensor. The information from these image sensors can be determined by interacting with electrical port 534. These image sensors can convert barcode images to electrical signals, which can be detected at port 534. In some embodiments, rack 530 is generally passive and unpowered. In these embodiments, power can be provided via electrical port 534 to power image sensors within the rack 520 to detect barcodes of tubes placed in the individual tube holders 532. In some embodiments, electrical port 534 provides a bus interface for interacting with image sensors in the rack 520. This bus interface may be any appropriate interface, such as a parallel or serial interface, such as an I2C bus or CAN bus.

Figure 14:
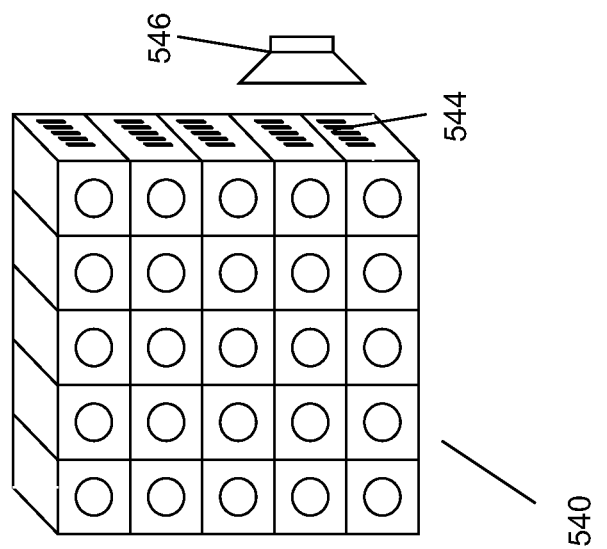
FIG. 14 is a perspective view of an array of exemplary tube holders for use with some embodiments disclosed herein.

FIG. 14 shows a two-dimensional rack 540 having a plurality of ports 544. These ports may be any of the ports described with reference to FIGS. 12 and 13. In some embodiments, image sensor 546 is used to observe optical ports. While racks are described herein as having individual tube holders, it should be appreciated that racks can be created by individual tube holders or monolithically, where tube holders share a common body.

Figure 15:
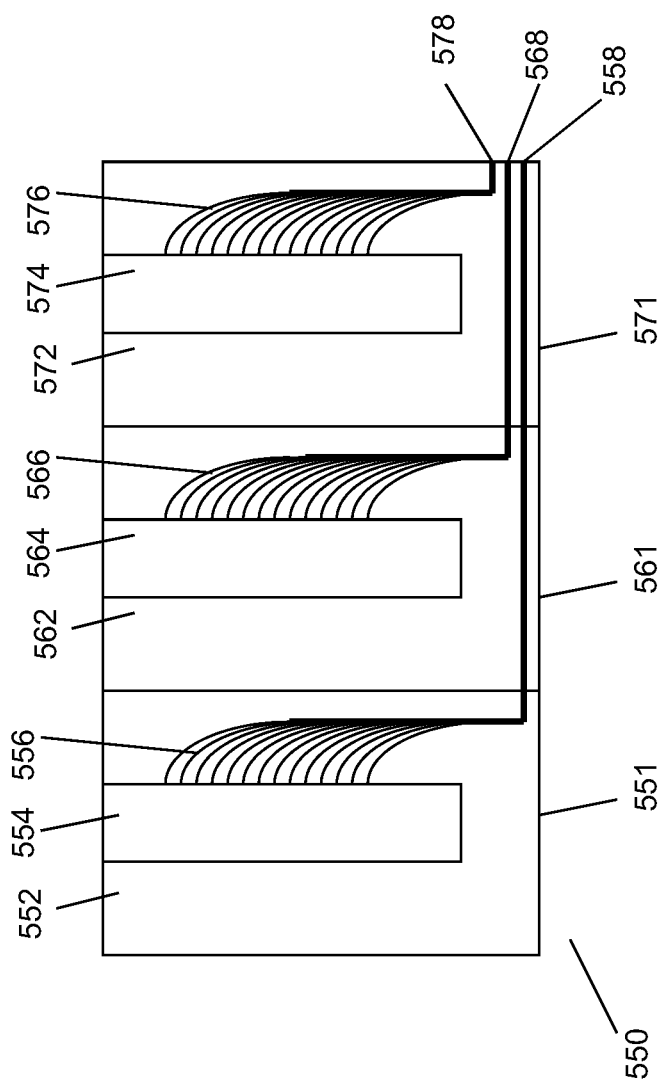
FIG. 15 is a perspective view of an array of exemplary tube holders for use with some embodiments disclosed herein.

FIG. 15 shows a cross-section of tube holders in a rack 550 employing an optical port. Tube holders 551, 561, and 571 include sidewalls 552, 562, and 572, respectively, and receiving portions 554, 564, and 574, respectively. Within the sidewalls 552, 562, and 572, optical bundles 556, 566, and 576, respectively, provide optical guides for propagation of image information from within the receiving portions to outputs 558, 568, and 578, respectively. In embodiments, optical bundles 556, 566, and 576 include fiber-optic fibers, which may be arranged in any suitable predetermined pattern. In some embodiments, the predetermined pattern includes fibers at multiple locations in the surface of each receiving portion to allow observation of a barcode in a broad range of orientations. In some embodiments, optical bundles 556, 566, and 576 include other optical paths, such as periscopic paths.

Barcodes may be read at different times at different locations of the automation system. In some embodiments, barcodes may be read at the insertion of a fluid container (e.g., sample tube) in a carrier or tray. The detection of the sample tube being inserted may be detected mechanically (e.g., depressing switch), electrically, and/or optically. Barcodes may also be read while at rest and/or during transport. For example, where carriers include passive optics, a reading station may be utilized to allow barcodes to be read after insertion while the carrier is on an automation track. The barcode of the payload of a carrier may be read at the testing station, updating the status change of the carrier payload. Similarly, a tray may be characterized after samples are inserted. Barcodes may also be read at predetermined intervals or continuously. Similarly, barcodes may be read on request. The request may be made automatically by the system or manually by a system operator. Carrier barcodes may be read at, or proximate to, a station. For example, during testing at a station, a sample tube may be removed from a carrier and/or a new tube may be inserted in the carrier.

Barcode information may be reported to a central controller at the time it is read or decoded, or at a later time. For example, a carrier or tray may scan barcode information and report the information (either raw data, such as images or sensor signals or decoded information) wirelessly immediately. In some embodiments, the carrier or tray may record the barcode information for later reporting. For example, a carrier or tray may report barcode information at regular intervals, at predetermined times, upon request (of the controller or operator), at certain locations, such as when a carrier approaches a decision point or when a tray is placed into an input lane of an analyzer.

It should be appreciated that the exemplary barcodes used in the illustrative embodiment need not be limited to linear barcodes. The systems described herein may be suitable or adaptable for use with two-dimensional and/or color barcodes. For example, in some embodiments, QR codes are used as barcode information. The term barcodes, therefore, can be considered to be a broad term to cover optical codes on the surface of an object. In some embodiments, the same mechanisms described for observing barcodes can be applied to observe other markings, such as writing on tubes. Accordingly, observation of any markings on the surfaces of sample tubes is encompassed by embodiments of the present invention.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A carrier configured to transport patient samples around an in vitro diagnostics automation system, the carrier comprising:
    a tube holder configured to hold a sample tube;
    one or more optical devices configured to receive an image of a barcode on the sample tube; and
    a reflective surface of the tube holder configured to reflect the image of the barcode to the one or more optical devices when the tube is in the tube holder in an orientation such that the barcode is not in a direct line of sight of the optical device.

2. The carrier of claim 1, wherein the reflective surface comprises a conical shaped internal surface of the tube holder.

3. The carrier of claim 1, wherein the reflective surface comprises a substantially parabolic shaped internal surface of the tube holder.

4. The carrier of claim 1, wherein the optical devices comprise one or more lenses.

5. The carrier of claim 1, wherein the optical devices comprise one or more imaging sensors.

6. The carrier of claim 1, wherein the optical devices comprise a light source and a photodetector.

7. The carrier of claim 1, further comprising a processor configured to receive barcode information from the one or more optical devices when the tube is inserted in the tube holder.

8. The carrier of claim 1, further comprising a processor configured to receive barcode information from the one or more optical devices in response to a request.

9. A carrier for use in an in vitro diagnostics environment comprising:
    a tube holder configured to hold a sample tube; and
    a plurality of optical devices configured to receive an image of a barcode on the sample tube, wherein the plurality of optical devices are arranged on a surface of the tube holder such that the barcode is in a line of sight of at least a portion of the plurality of optical devices.

10. The carrier of claim 9, wherein the surface of the tube holder comprises an internal surface, and the tube holder is configured to accept a tube such that the barcode is substantially within the tube holder.

11. The carrier of claim 9, wherein the surface of the tube holder comprises an external surface, and the tube holder is configured to accept a tube such that the barcode is substantially outside the tube holder.

12. The carrier of claim 9, wherein the optical devices comprise one or more lenses.

13. The carrier of claim 9, wherein the optical devices comprise one or more imaging sensors.

14. The carrier of claim 9, wherein the optical devices comprise a light source and a photodetector.

15. The carrier of claim 9, further comprising a processor configured to receive barcode information from the one or more optical devices when the tube is inserted in the tube holder.

16. The carrier of claim 9, further comprising a processor configured to receive barcode information from the one or more optical devices in response to a request.

17. A carrier configured to transport patient samples around an in vitro diagnostics automation system, the carrier comprising:
    a tube holder configured to hold a sample tube;
    one or more optical devices configured to receive an image of a barcode on the sample tube; and
    a rotation device configured to rotate the sample tube relative to the carrier to orient the barcode within a line of sight of at least one of the one or more optical devices.

18. The carrier of claim 17, wherein the rotation device comprises a gear.

19. The carrier of claim 17, wherein the rotation device interfaces an externally applied friction wheel.

20. The carrier of claim 17, wherein the rotation device comprises a motor.

21. The carrier of claim 17, wherein the optical devices comprise one or more lenses.

22. The carrier of claim 17, wherein the optical devices comprise one or more imaging sensors.

23. The carrier of claim 17, wherein the optical devices comprise a light source and a photodetector.

24. A rack for transporting samples around an in vitro diagnostics environment automation system, the rack comprising:
    a plurality of tube holders, each configured to hold a sample tube; and
    a plurality of optical paths within the structure of the rack for conveying images of each sample tube to one or more optical ports,
    wherein the one or more optical ports are suitable for observing barcode information associated with tubes placed in the plurality of tube holders.

25. The rack of claim 24, wherein the optical paths comprise one or more optical fibers.

26. A rack for transporting samples in an in vitro diagnostics environment comprising:
    a plurality of tube holders, each configured to hold a sample tube;
    a plurality of optical devices on one or more surfaces within the rack for observing barcodes of each sample tube; and
    an electrical port coupled to the plurality of optical devices for communicating images of the barcodes between the optical devices and the electrical port.

* * * * *